(12) United States Patent
Kawakita et al.

(10) Patent No.: US 10,258,777 B2
(45) Date of Patent: Apr. 16, 2019

(54) DRUG TREATMENT METHOD AND DELIVERY DEVICE

(71) Applicant: Terumo Kabushiki Kaisha, Tokyo (JP)

(72) Inventors: Taisei Kawakita, Fujinomiya (JP);
Tomoji Maruyama, Hadano (JP);
Ryota Tanetani, Fujinomiya (JP);
Hiroyuki Taguchi, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/424,364

(22) Filed: Feb. 3, 2017

(65) Prior Publication Data

US 2017/0239453 A1    Aug. 24, 2017

(30) Foreign Application Priority Data

Feb. 18, 2016    (JP) ................ 2016-029324

(51) Int. Cl.
*A61F 2/82* (2013.01)
*A61B 17/22* (2006.01)
*A61M 25/09* (2006.01)
*A61M 25/10* (2013.01)
*A61M 31/00* (2006.01)

(52) U.S. Cl.
CPC .......... *A61M 31/002* (2013.01); *A61M 25/09* (2013.01); *A61B 17/2202* (2013.01); *A61B 2017/22042* (2013.01); *A61B 2017/22084* (2013.01); *A61B 2017/22088* (2013.01); *A61F 2/82* (2013.01); *A61F 2250/0067* (2013.01); *A61M 25/10* (2013.01); *A61M 25/104* (2013.01); *A61M 2025/09008* (2013.01); *A61M 2025/09083* (2013.01); *A61M 2025/09166* (2013.01); *A61M 2025/09175* (2013.01); *A61M 2025/105* (2013.01); *A61M 2205/04* (2013.01); *A61M 2205/32* (2013.01); *A61M 2205/3673* (2013.01); *A61M 2205/3693* (2013.01)

(58) Field of Classification Search
CPC ................ A61M 31/002; A61M 25/10; A61M 2025/105; A61M 25/09
USPC .......................... 600/585; 604/20, 22, 891.1
See application file for complete search history.

(56) References Cited

U.S. PATENT DOCUMENTS

| 4,360,019 A * | 11/1982 | Portner ............. A61M 5/14276 604/131 |
| 2007/0141112 A1 | 6/2007 | Falotico et al. |
| 2008/0097281 A1* | 4/2008 | Zusman ............ A61M 37/0092 604/22 |

FOREIGN PATENT DOCUMENTS

JP    2007-190369    8/2007

* cited by examiner

*Primary Examiner* — Theodore J Stigell
(74) *Attorney, Agent, or Firm* — Jason H. Vick; Sheridan Ross, PC

(57) ABSTRACT

Provided is a treatment method and a medical device that can intentionally and locally administer a drug to a lesion area appearing in a narrow blood vessel such as a retinal blood vessel and a spinal blood vessel. The treatment method has an introduction step of introducing a medical elongated body having a drug holder for holding a drug into a living body, an arrangement step of arranging the drug holder at a treatment target inside the living body, and a discharge step of discharging the drug to the treatment target by releasing the drug held by the drug holder.

20 Claims, 14 Drawing Sheets

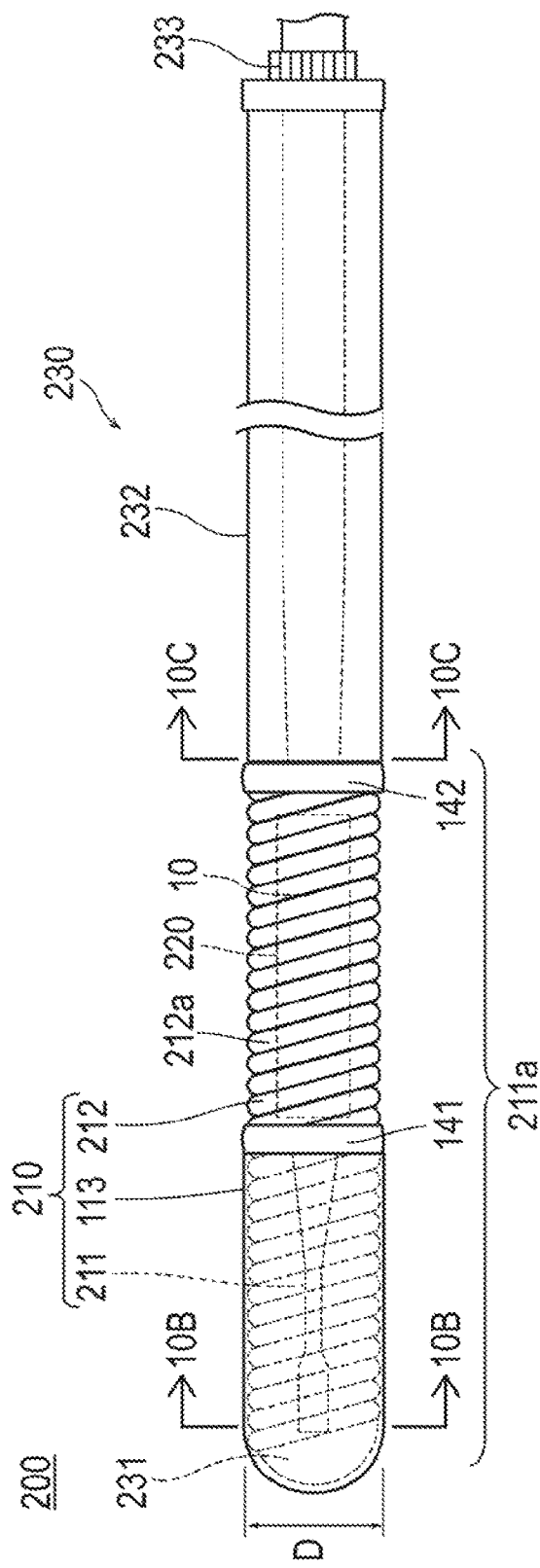
FIG. 10A
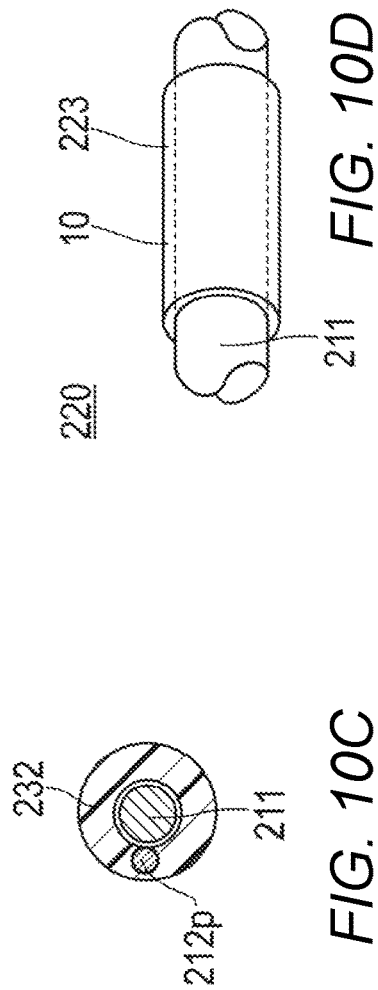
FIG. 10D
FIG. 10C
FIG. 10B

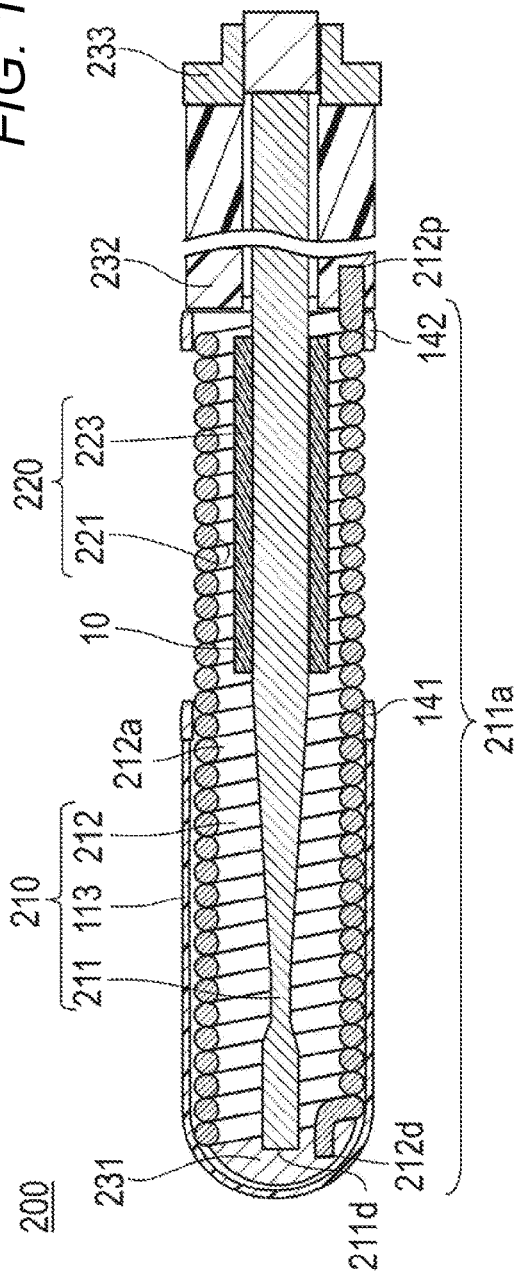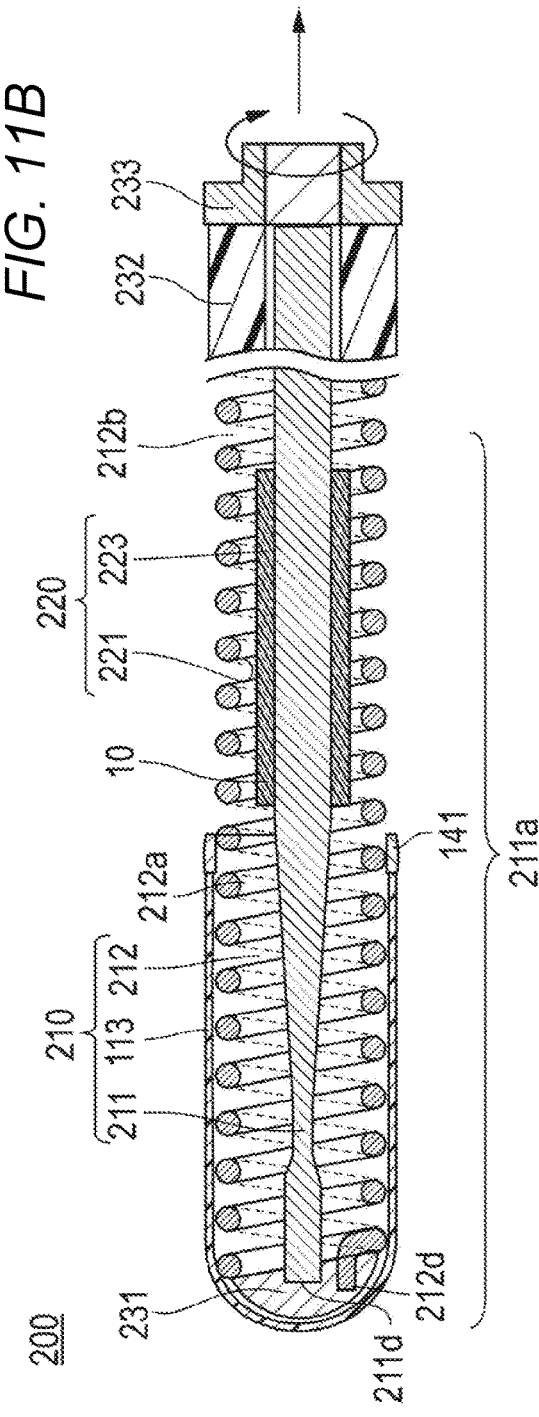

DRUG TREATMENT METHOD AND DELIVERY DEVICE

CROSS REFERENCE TO RELATED APPLICATIONS

The present application claims the benefit of priority, under 35 U.S.C. § 119(e), to Japanese Application No. 2016-029324, filed Feb. 18, 2016, entitled "How Treatment, and Medical Equipment," the entire disclosure of which is incorporated herein by reference in its entirety, for all that it teaches and for all purposes.

TECHNICAL FIELD

The present invention relates to a treatment method of administering a drug to a treatment target inside a living body, and a medical device which administers the drug to the treatment target inside the living body.

BACKGROUND ART

Traditionally, the treatment of stenosis or an occlusion in a blood vessel involves technique in which a catheter device, such as a balloon catheter and a stent delivery system, is used to administer a drug to the stenosed site.

However, the above-described catheter device is not suited for insertion into a narrow blood vessel such as a retinal blood vessel and a spinal blood vessel. Consequently, the catheter device has not been applicable to narrow blood vessels. A treatment method and a medical instrument have not been previously disclosed in which a drug can be locally administered to a lesion area appearing in a narrow blood vessel such as the retinal blood vessel and/or a spinal blood vessel.

For example, Patent Application No. JP-A-2007-190369, the entire contents of which are hereby incorporated herein by reference for all that it teaches and for all purposes, discloses a medical device in which a drug is carried by a guide wire that is generally used for guiding a catheter into a living body.

SUMMARY

A guide wire has a cross-sectional diameter smaller than that of a catheter, and can be inserted into a narrow blood vessel such as a retinal blood vessel and/or a spinal blood vessel. Accordingly, a guide wire may be configured to deliver a drug into narrow blood vessels such as the retinal blood vessels and/or spinal blood vessels.

However, the guide wire of Patent Application No. JP-A-2007-19036 above, is required to indwell in a living body for a long time until the drug carried by the guide wire is naturally eluted, thereby causing a patient to bear a serious burden. Therefore, it is desirable to introduce a treatment method which allows for the selective and intentional discharge of the drug using a balloon catheter or a stent delivery system.

The present disclosure is made in view of the above-described problem, and an object thereof is to provide a treatment method and a medical device which can intentionally and locally administer a drug to a lesion area appearing in a narrow blood vessel such as a retinal blood vessel and/or a spinal blood vessel.

Solution to the Problem

In some embodiments, a treatment method according to the present disclosure has an introduction step of introducing a medical elongated body having a drug holder for holding a drug into a living body, an arrangement step of arranging the drug holder at a treatment target inside the living body, and a discharge step of discharging the drug to the treatment target by releasing the drug held by the drug holder.

In some embodiments, it is an object of the present disclosure to provide a medical device having a medical elongated body that includes a drug holder for holding a drug, and that extends along an axial direction, and a releasing unit that releases the drug held by the drug holder.

Advantageous Effects

According to embodiments of the above-described treatment method, the drug, in a held state, may be delivered to the treatment target. Accordingly, the drug is not unintentionally discharged to a site other than a treatment target inside the living body, and the drug can be locally administered to the treatment target. Therefore, the treatment target can be more effectively treated. Furthermore, according to a treatment method of the present disclosure, after the drug holder is arranged at the treatment target, the drug held by the drug holder may be selectively released so as to intentionally discharge the drug to the treatment target. Therefore, the drug can be administered to the treatment target at a desired timing.

According to the medical device configured as described above, a skilled technique using the medical elongated body having the drug holder arranged therein and the releasing unit enables the drug to be locally administered to the treatment target. Therefore, the treatment target can be more effectively treated. In addition, the medical device includes the releasing unit which releases the held drug. Therefore, the drug can be administered to the treatment target at a desired timing.

BRIEF DESCRIPTION OF THE DRAWINGS

FIG. 10A is a schematic view illustrating a medical device in accordance with embodiments of the present disclosure.

FIG. 10B is a cross-sectional view taken along line 10B-10B shown in FIG. 10A.

FIG. 10C is a cross-sectional view taken along line 10C-10C shown in FIG. 10A.

FIG. 10D is a perspective view of an embodiment of a drug holder.

FIG. 11A is a cross-sectional view of an embodiment of the medical device.

FIG. 11B is a cross-sectional view illustrating an operation of a releasing unit of the medical device shown in FIG. 11A.

DETAILED DESCRIPTION

Figure 1:
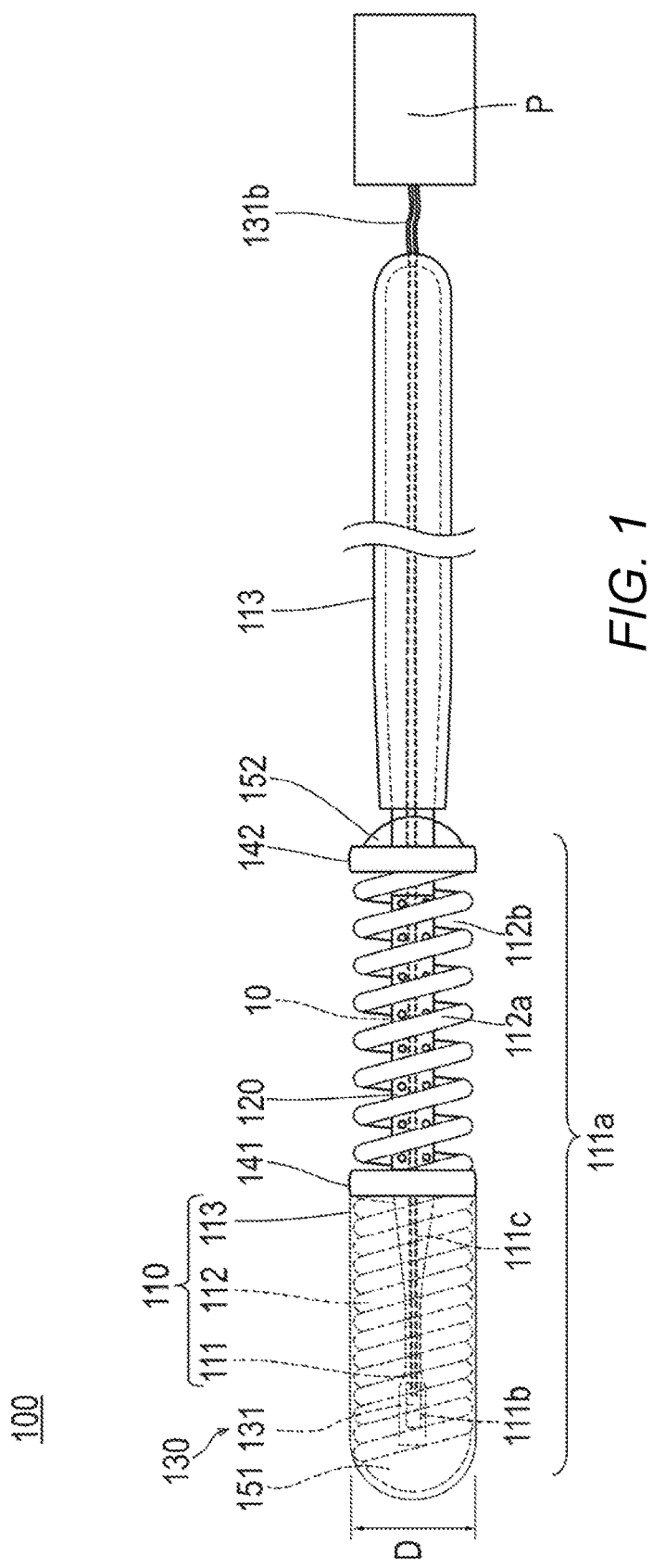
FIG. 1 is a schematic view illustrating an embodiment of a medical device.

Hereinafter, embodiments of the present disclosure will be described with reference to the drawings. The following description does not limit the technical scope or the meaning of terms disclosed in the appended claims. In some cases, a dimension ratio in the drawings may be exaggerated and different from a ratio used in practice in order to facilitate the description.

Figure 3:
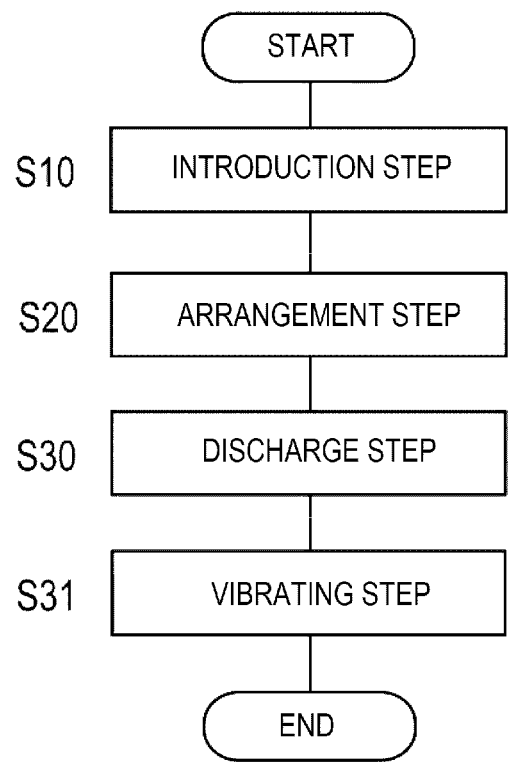
FIG. 3 is a flowchart illustrating a treatment method in accordance with embodiments of the present disclosure.
Figure 4:
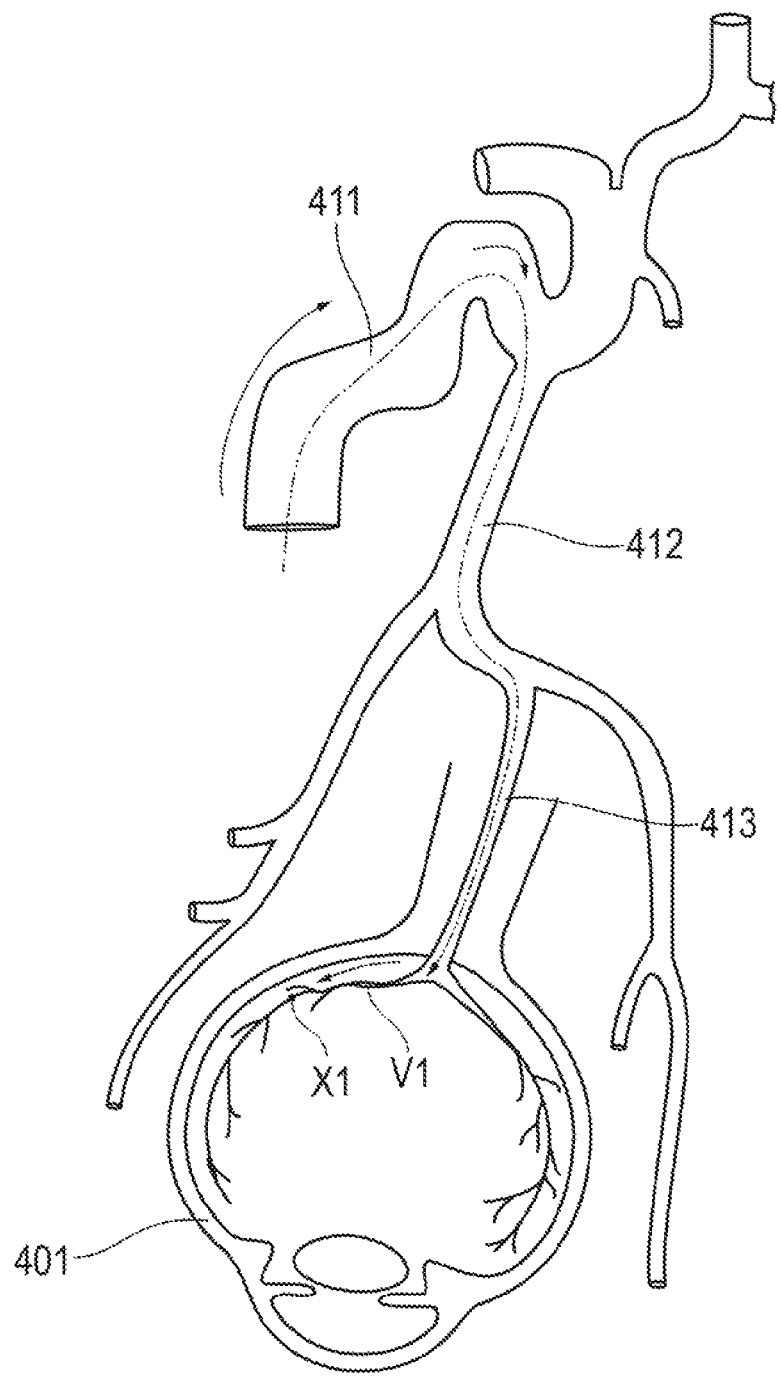
FIG. 4 is a schematic view illustrating apart of a living body to which embodiments of the treatment method may be applied.

FIGS. 1 and 2 are views describing a configuration of a medical device 100 in accordance embodiments of the present disclosure. FIG. 3 is a flowchart illustrating a treatment method in accordance with embodiments of the present disclosure. FIGS. 4 and 7 are schematic views illustrating a part of a living body 400 to which embodiments of the treatment method may be applied. FIGS. 5, 6, 8, and 9 are views illustrating a treatment method in accordance with embodiments of the present disclosure.

In some embodiments a treatment method is described for treating a lesion area. As illustrated in FIGS. 6 and 9, for example, a drug in a held state is delivered to a lesion area in which a stenosis or an occlusion has developed in a very narrow blood vessel, such as a retinal artery V1 and/or a spinal artery V2. The drug may be locally discharged to the lesion area by selectively and intentionally releasing the held drug.

Referring to FIGS. 1 and 2, a medical device 100 used for the treatment methods according to embodiments of the present disclosure will be described.

As illustrated in FIG. 1, the medical device 100 has a medical elongated body 110 that includes a drug holder 120 for holding a drug 10, and that extends along an axial direction, and a releasing unit 130 that includes a vibrating portion 131 for releasing the held drug 10 by vibrating the drug holder 120. A first marker 141 and a second marker 142 which are respectively provided with X-ray contrast capability are arranged on a distal side and a proximal side of the drug holder 120. In addition, the vibrating portion 131 may be electrically connected to an external device (power source) P which transmits an electric signal.

In this description, a side inserted into the living body 400 is referred to as a "distal side", a side opposite to the distal side is referred to as a "proximal side", and an extending direction of the medical elongated body 110 is referred to as the axial direction. In addition, a distal portion means a fixed range including a distal end (distal-most end) and a peripheral portion thereof. A proximal portion means a fixed range including a proximal end (proximal-most end) and a peripheral portion thereof.

The medical elongated body 110 and the drug holder 120 will be described.

The medical elongated body 110 has a core 111 which extends along the axial direction and a flexible portion 112 which is arranged in a distal portion 111a of the core 111. In addition, a covering layer 113 which covers a portion other than a portion having the drug holder 120 disposed therein is disposed on an outer surface of the medical elongated body 110.

In the medical elongated body 110, a cross-sectional outer shape of a portion inserted into the living body may be substantially circular, and that a diameter D thereof may be 0.2 to 0.5 mm. In this embodiment, the cross-sectional diameter D of the medical elongated body 110 is very small compared to the cross-sectional diameter of a balloon catheter or a stent delivery system that is generally used for percutaneous transluminal coronary angioplasty (PTCA). Accordingly, the medical elongated body 110 can perform predetermined treatment after being inserted into a narrow blood vessel, for example, such as the retinal artery V1 and/or the spinal artery V2.

The core 111 is an elongated member which extends along the axial direction. In some embodiments, the core 111 includes a flat plate portion 111b which is formed in the distal end, and a tapered portion 111c which is formed on the proximal side of the flat plate portion 111b and which has a shape tapered toward the distal side. An operator may deform the flat plate portion 111b, thereby enabling the distal portion of the medical elongated body 110 to have a desired shape (to be reshaped). In addition, since the tapered portion 111c is provided therein, rigidity can be gradually reduced toward the distal side of the medical elongated body 110, and the distal portion 111a of the core 111 is enabled to have satisfactory flexibility. The core 111 does not necessarily include the tapered portion 111c and the flat plate portion 111b. For example, the core 111 may be configured to include a rod-shaped member having an outer shape which is constant from the proximal side toward the distal side.

A material configuring the core 111 is not particularly limited as long as the material is provided with flexibility and rigidity to such a degree that the core 111 can follow a biological lumen which may be meandering or curved. It is possible to use a known resin material or metal material. For example, the metal material includes stainless steel, spring steel, titanium, tungsten, tantalum, and a super-elastic alloy such as a nickel-titanium alloy. For example, the resin material includes polyimide resins, polyamide resins, polyester resins, polycarbonate resins, and composite materials in which these resins are combined with a reinforcing fiber such as a glass fiber.

Figure 2A:
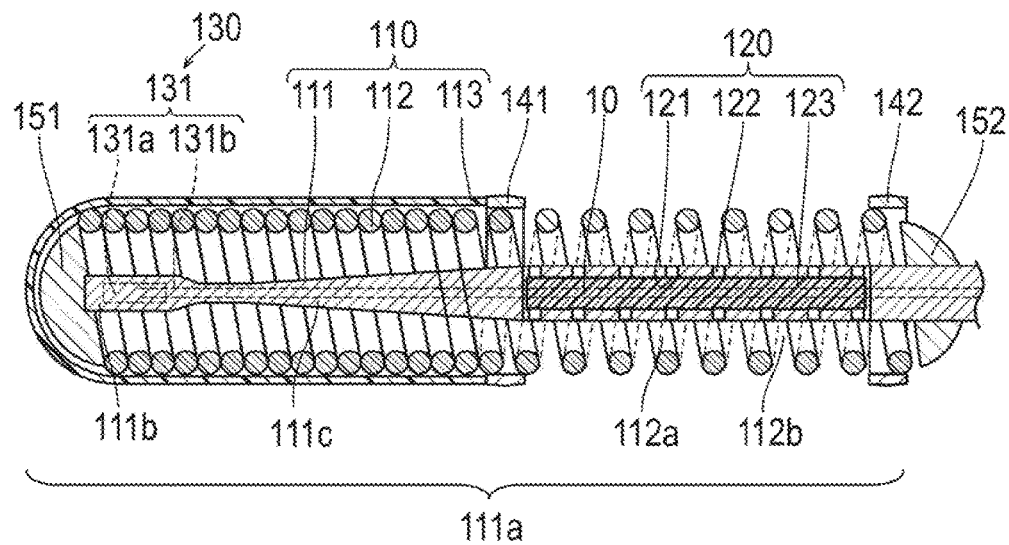
FIG. 2A is a cross-sectional view of an embodiment of the medical device.

As illustrated in FIG. 2A, the drug holder 120 is arranged in the distal portion 111a of the core 111.

The drug holder 120 is configured to include an accommodation space 121 which is formed in a lumen of the core 111, a hole portion 122 which causes accommodation space 121 and the outer surface of the core 111 to communicate with each other, and a drug carrier 123 which holds the drug 10.

Figure 2B:
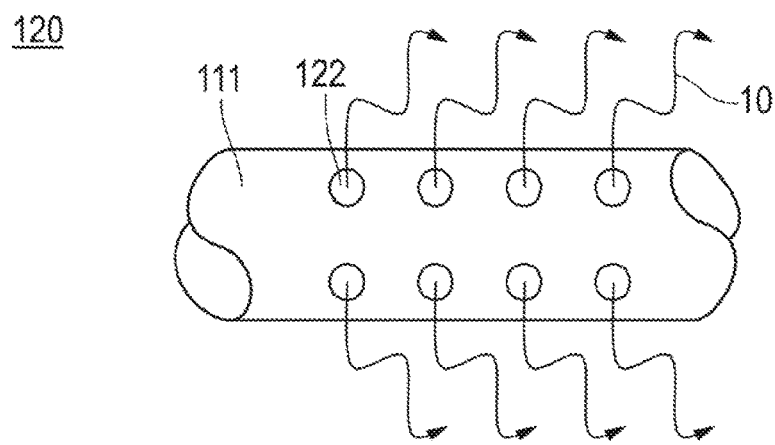
FIG. 2B is a view of an embodiment of a drug holder.

The drug 10 in a state of being carried by the drug carrier 123 is held inside the accommodation space 121. As illustrated in FIG. 2B, if the drug carrier 123 is decomposed, the drug 10 is discharged (sustainably released) to the outside of the accommodation space 121 via the hole portion 122.

The drug 10 is not particularly limited as long as the drug 10 is suitable for a lesion area which is a treatment target, and can be optionally selected. Specifically, the drug includes anti-cancer agents, limus-based immunosuppressive agents, antibiotics, anti-thrombotic drugs, HMG-CoA reductase inhibitors, ACE inhibitors, calcium antagonists, anti-hyperlipidemic agents, integrin inhibitors, anti-allergic agents, anti-oxidants, GPIIbIIIa antagonists, retinoids, lipid improving agents, anti-platelet drugs, and anti-inflammatory drugs.

In some embodiments, the drug carrier 123 material may be a polymeric material. In particular, a biodegradable polymer, which may be configured to decompose inside the living body 400, may be used. As the biodegradable polymer material, for example, it is possible to use biodegradable synthetic polymer materials such as polylactic acid, polyglycolic acid, lactic-glycolic acid copolymer, polycaprolactone, lactic acid-caprolactone copolymer, glycolic acid-caprolactone copolymer, and poly-γ-glutamic acid, or natural biodegradable polymer materials such as cellulose and collagen.

The flexible portion 112 may be formed in a coil shape in which a linear member 112a is spirally wound along an outer peripheral surface of the core 111 extending along the axial direction. The linear member 112a may be wound so as to form a gap 112b which causes the inside and the outside of the flexible portion 112 to communicate with each other, in a portion having the drug holder 120 arranged therein.

The flexible portion 112 may be formed of a flexible material, and is deformable along the biological lumen which is meandering or curved. The flexible portion 112 may be provided with a function to guide the movement of the medical elongated body 110 in the biological lumen.

A material configuring the linear member 112a is not particularly limited as long as the material is flexible. For example, a known metal material or resin material can be used. As the metal material, it is possible to use stainless steel, a noble metal such as Gold (Au) or Platinum (Pt), or an alloy of these materials. The flexible portion 112 may be entirely formed of the same material, or the distal portion may be formed of a material which is more flexible than that of the proximal portion.

The distal end and the proximal end of the core 111 and the flexible portion 112 are respectively fixed (fixedly attached) to a distal side fixing portion 151 and a proximal side fixing portion 152. In this manner, the core 111, the flexible portion 112, and the flexible portion 112 can be integrally formed. Therefore, it is possible to improve mechanical strength of the medical device 100. Although a fixing method is not particularly limited, it is possible to use a method such as brazing, soldering, bonding using an adhesive, and/or welding.

The covering layer 113 may be configured to include a material which is flexible and which can reduce friction. In this manner, the covering layer 113 becomes flexible, thereby enabling the medical elongated body 110 to be inserted into the body without damaging an inner wall of the living body 400 such as blood vessels. In addition, frictional resistance (sliding resistance) against an inner surface of a catheter, for instance when the medical elongated body 110 is inserted into the body, may be reduced, thereby improving sliding performance and achieving more satisfactory operability.

As a material for configuring the covering layer 113, for example, it is possible to use polyolefin resins such as polyethylene resins and polypropylene resins, polyvinyl chloride resins, polyester resins (PET, or PBT), polyamide resins, polyimide resins, polyurethane resins, polystyrene resins, polycarbonate resins, silicone resins, fluorine resins (PTFE, or ETFE), or a composite material of these materials.

Without being limited to a configuration including the flexible portion 112, the medical elongated body 110 may adopt a configuration without including the flexible portion 112.

The first marker 141 and the second marker 142 have a ring shape (cylindrical shape). Both of these in a state of being fitted to and inserted into the flexible portion 112 are respectively fixed to the distal side and the proximal side of the drug holder 120. Each position on the distal side and the proximal side of the drug holder 120 can be clearly confirmed by confirming each position of the first marker 141 and the second marker 142 on an X-ray image. Therefore, the drug holder 120 can be relatively easily positioned at a position of the lesion area.

The first marker 141 and the second marker 142 are not limited to the above-described configuration, as long as a portion provided with the X-ray contrast capability can be arranged on the distal side and the proximal side of the drug holder 120. For example, a configuration may be adopted in which the portion provided with the X-ray contrast capability is formed in a portion of the flexible portion 112 or the core 111.

For example, a material configuring the first marker 141 and the second marker 142 can be configured to include a material provided with the X-ray contrast capability, and can also be configured so that a resin material having no X-ray contrast capability covers or contains a material provided with the X-ray contrast capability. As the material provided with the X-ray contrast capability, for example, it is possible to use metal such as platinum, gold, silver, iridium, titanium, and tungsten, or an alloy of these materials.

Without being limited to the configuration including the first marker 141 and the second marker 142, for example, a configuration may be adopted in which a marker function is provided in such a way that a portion of the flexible portion 112 arranged on the distal side and the proximal side of the drug holder 120 is formed of the material provided with the X-ray contrast capability.

The vibrating portion 131 included in the releasing unit 130 will be described.

Figure 2C:
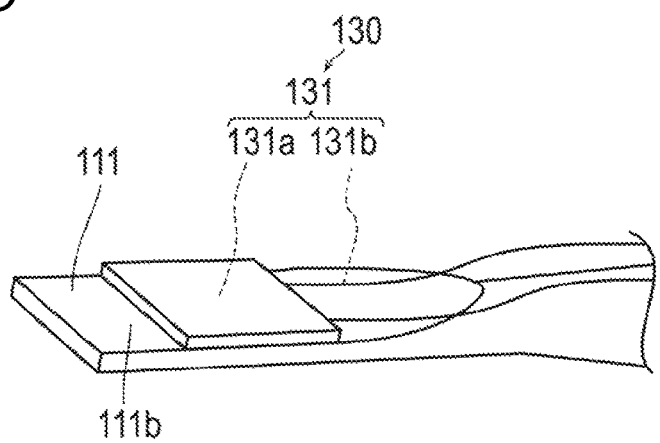
FIG. 2C is a view of an embodiment of a releasing unit.

As illustrated in FIG. 2C, the vibrating portion 131 may include an oscillator 131a and an electric wire 131b which electrically connects the oscillator 131a and the external device P to one another.

An electric signal may be applied to the oscillator 131a in a state where the external device P is operated and power is supplied to the electric wire 131b. If the electric signal is applied to the oscillator 131a, ultrasound vibrations may be generated due to a piezoelectric effect. The vibrations generated by the oscillator 131a are not limited to the ultrasound vibrations.

In some embodiments, the oscillator 131a is arranged to come into contact with the flat plate portion 111b of the core 111. The oscillator 131a may be arranged in the flat plate portion 111b, thereby increasing a contact surface between the oscillator 131a and the core 111. Accordingly, the vibrations generated by the oscillator 131a can be efficiently transmitted to the core 111.

As a material configuring the oscillator 131a, for example, it is possible to use a piezoelectric material such as ceramics and/or quartz.

Next, referring to FIGS. 3 to 9, a treatment method is described in accordance with embodiments of the present disclosure. Hereinafter, an example will be described in which two portions of the retinal artery V1 and the spinal artery V2 serve as a treatment target site in the living body 400 to which the treatment method may be applied.

Referring now to FIGS. 3 to 6, a treatment method is described in which a stenosed site X1 developed in the retinal artery V1 serves as the treatment target.

As illustrated in FIG. 3, in brief, the treatment method has an introduction step (S10), an arrangement step (S20), and a discharge step (S30). Hereinafter, each step will be sequentially described.

In the introduction step (S10), the medical elongated body 110 having the drug holder 120 arranged therein is introduced into the stenosed site X1 of the retinal artery V1. Referring to FIG. 4, for example, the medical elongated body 110 can be introduced into the retinal artery V1 in an eyeball 401 by way of an internal carotid artery 411, an ophthalmic artery 412, and a central retinal artery 413 in this order. Hereinafter, a specific procedure in the introduction step (S10) will be described.

First, a guide wire GW is inserted into the internal carotid artery 411 located in the vicinity of a neck base. Specifically, first, an introducer 20 is inserted into a perforation formed in a wrist using a medical instrument such as a surgical scalpel. Next, the guide wire GW is inserted into the internal carotid artery 411 via the introducer 20.

Figure 5:
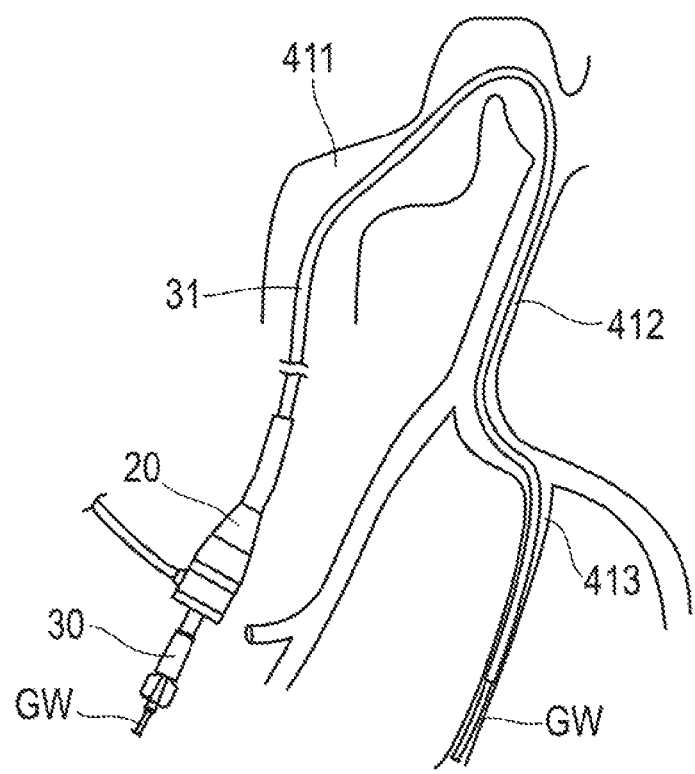
FIG. 5 is a schematic view illustrating an embodiment of the treatment method.

Next, as illustrated in FIG. 5, the guide wire GW is moved ahead, and is inserted into the central retinal artery 413 through the internal carotid artery 411 and the ophthalmic artery 412. A sheath 31 of a micro-catheter 30 is inserted into the central retinal artery 413 along the guide wire GW.

Figure 6A:
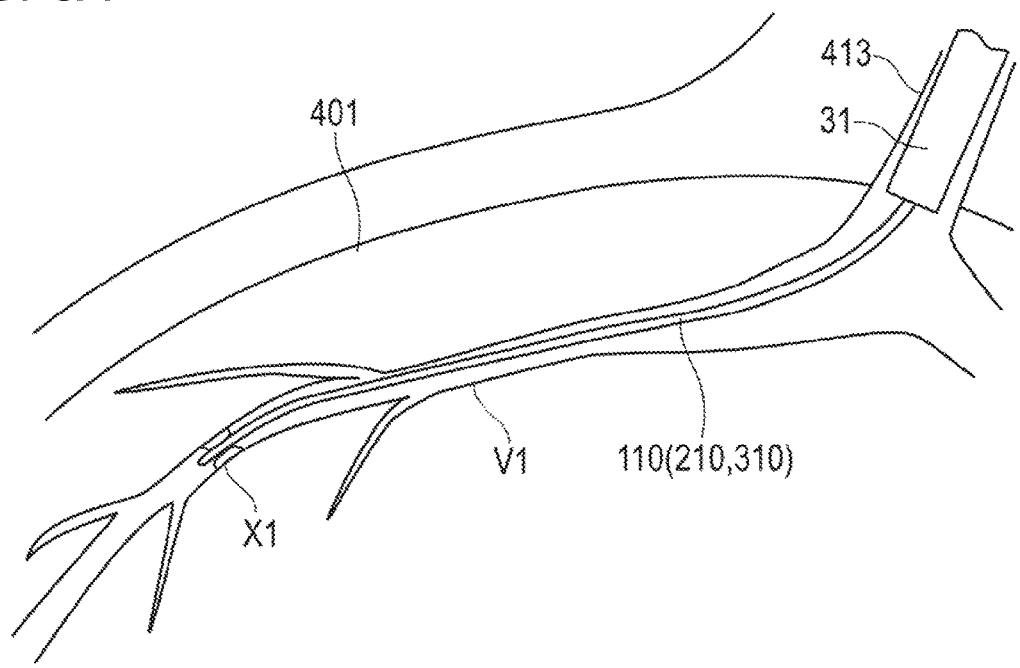
FIG. 6A is a first schematic view illustrating a treatment method in accordance with embodiments of the present disclosure.
Figure 7:
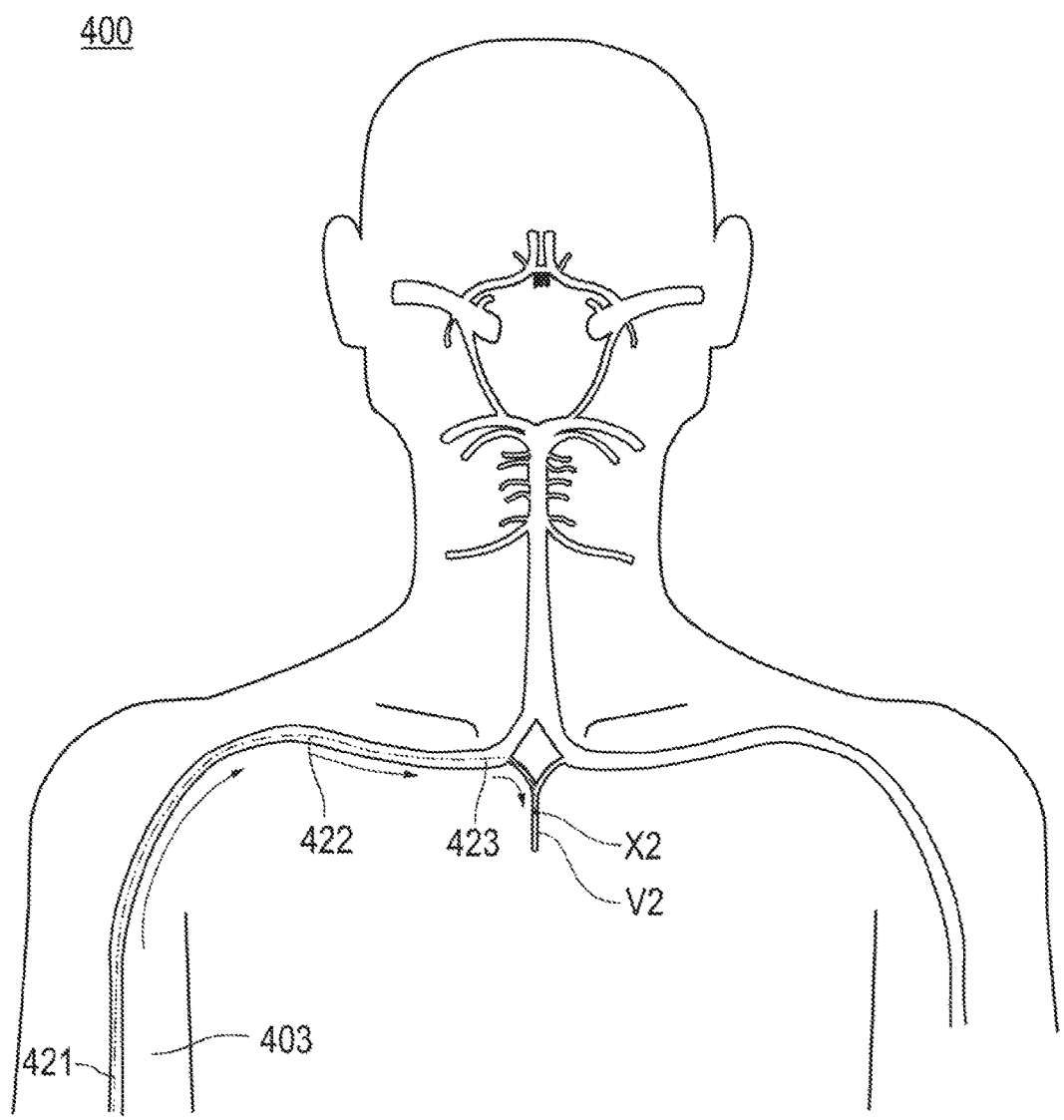
FIG. 7 is a schematic view illustrating a part of the living body to which a treatment method may be applied in accordance with embodiments of the present disclosure.

Next, as illustrated in FIG. 6A, the guide wire GW is removed therefrom. Via the lumen of the sheath 31 of the micro-catheter 30, the medical elongated body 110 is inserted into the stenosed site X1 of the retinal artery V1 through the internal carotid artery 411, the ophthalmic artery 412, and the central retinal artery 413.

Figure 6B:
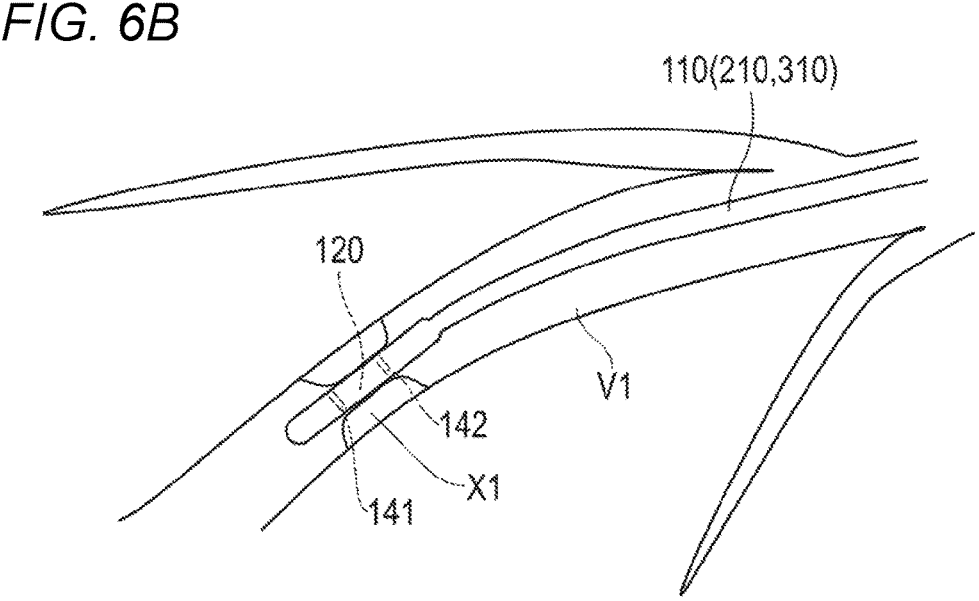
FIG. 6B is a second schematic view illustrating a treatment method in accordance with embodiments of the present disclosure.

Next, in the arrangement step (S20), as illustrated in FIG. 6B, the drug holder 120 is positioned and arranged at the stenosed site X1. At this time, while the position of the first marker 141 and the second marker 142 is confirmed using the X-ray image acquired through X-ray radiography, the position of the drug holder 120 is adjusted. In this manner, it is possible to relatively easily perform the positioning of the drug holder 120.

Next, in the discharge step (S30), the drug 10 is discharged to the stenosed site X1 by releasing the drug 10 held by the drug holder 120. Specifically, in the discharge step (S30), a vibrating step (S31) of vibrating the drug holder 120 is performed.

In the vibrating step (S31), the external device P is operated, and power is supplied to the electric wire 131b, thereby applying the electric signal to the oscillator 131a. In this manner, the oscillator 131a generates vibrations, thereby vibrating the core 111 to come into contact with the oscillator 131a. The core 111 is vibrated, thereby vibrating the drug holder 120. The vibrations are propagated to the drug holder 120, and vibration energy promotes decomposition of the drug carrier 123 which carries the drug 10.

Thus, the drug 10 is eluted. At this time, an elution rate of the drug 10 can be controlled by controlling the amplitude or the vibration frequency generated by the oscillator 131a. Specifically, as the amplitude or the vibration frequency increases, the elution rate of the drug 10 increases. If the amplitude or the vibration frequency decreases, the elution rate decreases.

Furthermore, the vibrations can be used to selectively control the discharge of the drug 10 from the drug holder 120. As illustrated in FIG. 2B, the drug 10 eluted inside the accommodation space 121 is discharged (sustainably released) to the outside of the accommodation space 121 via the hole portion 122. According to the above-described procedure, the drug 10 is completely administered to the stenosed site X1.

After the drug 10 is completely administered to the stenosed site X1, the medical elongated body 110, the micro-catheter 30, and the introducer 20 are removed therefrom. For example, another medical instrument may be delivered to the stenosed site X1 along the medical elongated body 110. In this manner, without removing these, the process may proceed to subsequent treatment. In addition, after the treatment is completed, the perforation formed as an introduction portion of the medical elongated body 110 or the introducer 20 is subjected to suitable hemostasis by means of sewing.

Next, referring to FIGS. 3 and 7 to 9, a treatment method will be described in which a stenosed site X2 developed in the spinal artery V2 serves as the treatment target.

The treatment method of the spinal artery V2 has three Steps S10 to S30, similar to the steps of the treatment method of the retinal artery V1 described above (refer to FIG. 3). A specific skilled technique demonstrated in the introduction step (S10) may be different from that of the above-described treatment method of the retinal artery V1. In other Steps S20 and S30, the skilled technique is demonstrated similarly to the above-described treatment method of the retinal artery V1. Thus, description of the similar steps previously described in the above specific skilled technique will be omitted.

In the introduction step (S10), the medical elongated body 110 having the drug holder 120 arranged therein is introduced into the stenosed site X2 of the spinal artery V2. Referring to FIG. 7, the medical elongated body 110 can be introduced into the spinal artery V2, for example, by way of the right radial artery 421, the right subclavian artery 422, and the vertebral artery 423 in this order. Hereinafter, a specific procedure in the introduction step (S10) will be described.

Figure 8A:
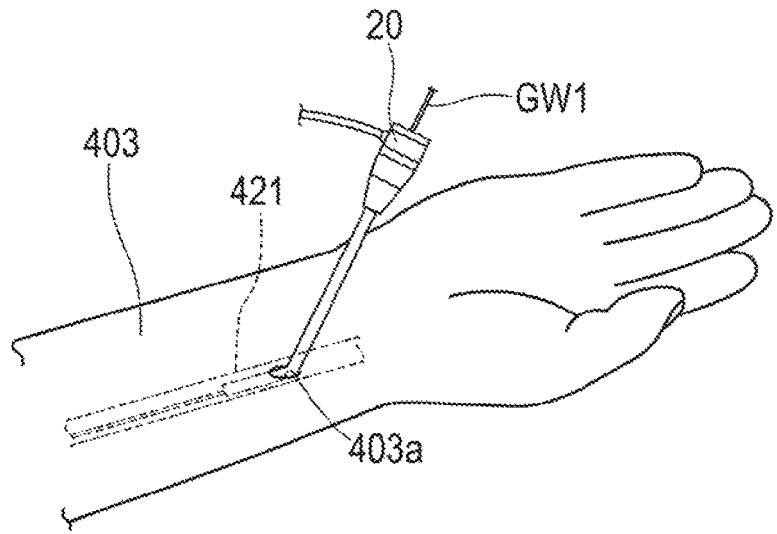
FIG. 8A is a first schematic view illustrating a treatment method in accordance with embodiments of the present disclosure.

First, as illustrated in FIG. 8A, the guide wire GW1 is inserted into a right radial artery 421 located at a right arm 403. Specifically, first, the introducer 20 is introduced toward the right radial artery 421 from the skin of the right arm 403 via a perforation 403a formed using a medical instrument such as a surgical scalpel. Next, the guide wire GW1 is inserted into the right radial artery 421 via the introducer 20.

Next, the guide wire GW1 is progressively moved to the right subclavian artery 422 from the right radial artery 421.

Figure 8B:
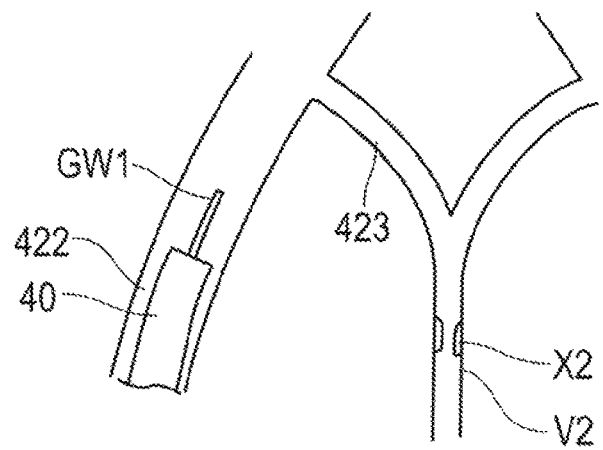
FIG. 8B is a second schematic view illustrating a treatment method in accordance with embodiments of the present disclosure.

Next, as illustrated in FIG. 8B, a guiding catheter 40 is inserted into the right subclavian artery 422 from the right radial artery 421 along the guide wire GW1, and is caused to indwell.

Next, via the lumen of the guiding catheter 40, the sheath 31 of the micro-catheter 30 is inserted into the right subclavian artery 422 from the right radial artery 421 along the guide wire GW1. Thereafter, the guide wire GW1 is removed therefrom.

Figure 8C:
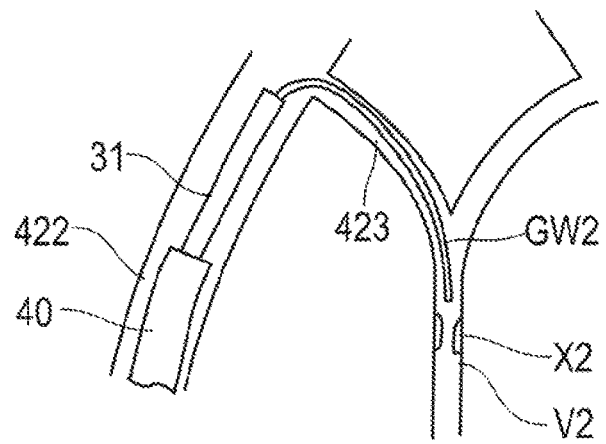
FIG. 8C is a third schematic view illustrating a treatment method in accordance with embodiments of the present disclosure.

Next, as illustrated in FIG. 8C, via the sheath 31 of the micro-catheter 30, the guide wire GW2 is inserted into the spinal artery V2 through the right subclavian artery 422 and the vertebral artery 423.

Figure 9A:
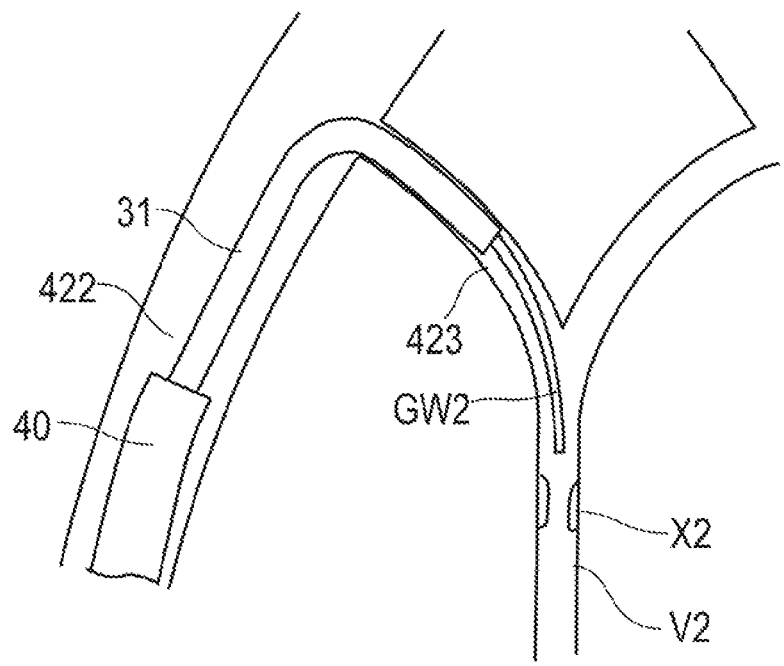
FIG. 9A is a fourth schematic view illustrating a treatment method in accordance with embodiments of the present disclosure.

Next, as illustrated in FIG. 9A, the sheath 31 of the micro-catheter 30 is inserted into the spinal artery V2 through the right subclavian artery 422 and the vertebral artery 423 along the guide wire GW2 which is inserted ahead.

Figure 9B:
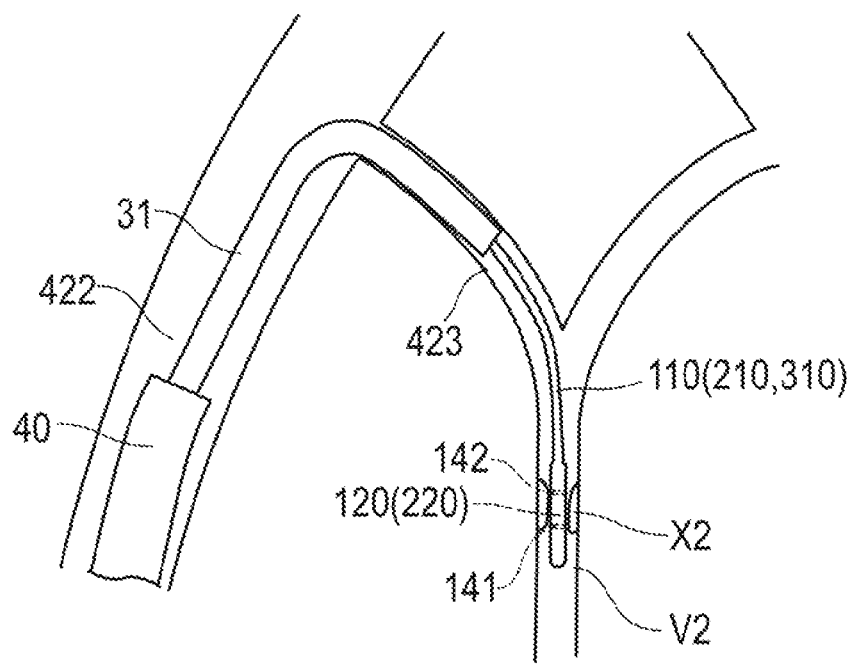
FIG. 9B is a fifth schematic view illustrating a treatment method in accordance with embodiments of the present disclosure.

Next, the guide wire GW2 is removed therefrom. As illustrated in FIG. 9B, via the lumen of the sheath 31 of the micro-catheter 30, the medical elongated body 110 is inserted into the stenosed site X2 in the spinal artery V2.

Next, the drug 10 may be completely administered to the stenosed site X2 through the arrangement step (S20) and the discharge step (S30).

Next, an operation effect according to embodiments of the present disclosure will be described.

In some embodiments, the treatment method may include the introduction step (S10) in which the drug holder 120 for holding the drug 10 is arranged, the arrangement step (S20) in which the drug holder 120 is arranged at the stenosed sites X1 and X2 which are the treatment targets inside the living body 400, and the discharge step (S30) in which the drug held by the drug holder 120 is released so as to be discharged to the stenosed sites X1 and X2.

According to the above-described treatment method, the drug 10 in a held state is delivered to the stenosed sites X1 and X2. Accordingly, the drug 10 is not unintentionally discharged to a site other than the stenosed sites X1 and X2 inside the living body 400, and the drug 10 can be locally administered to the stenosed sites X1 and X2. Therefore, the stenosed sites X1 and X2 can be more effectively treated. Furthermore, after the drug holder 120 is arranged at the stenosed sites X1 and X2, the drug 10 held by the drug holder 120 may be selectively released so as to intentionally discharge the drug 10 to the stenosed sites X1 and X2. Therefore, the drug 10 can be administered to the stenosed sites X1 and X2 at a desired timing.

In addition, according to the treatment methods described herein, in the discharge step, the drug 10 is discharged to the stenosed sites X1 and X2 which are the treatment targets, by vibrating the drug holder 120. Vibration energy generated by the vibrated drug holder 120 can promote decomposition of the drug carrier 123 which carries the drug 10. Accordingly, the drug 10 can be quickly eluted. In addition, the drug 10 can be discharged (sustainably released) to the outside of the drug holder 120 by utilizing the vibrations. Therefore, the drug 10 can be administered to the stenosed site X1 at desired timing.

In addition, in the medical elongated body 110, the cross-sectional outer shape of the portion inserted into the living body may be substantially circular, and the cross-sectional diameter D may be 0.2 to 0.5 mm. In this way, the cross-sectional diameter D of the medical elongated body 110 is relatively small. Accordingly, the medical elongated body 110 can perform predetermined treatment by being inserted into the narrow blood vessel into which a medical device is less likely to be inserted, for example, such as the retinal artery V1 and the spinal artery V2.

In addition, the medical device 100 may have the medical elongated body 110 that includes the drug holder 120 for holding the drug, and that extends along the axial direction, and the releasing unit 130 which releases the drug held by the drug holder 120.

According to the above-described medical device 100, a skilled technique using the medical elongated body 110 having the drug holder 120 arranged therein and the releasing unit 130 enables the drug 10 to be locally and selectively administered to the stenosed sites X1 and X2 which are the treatment targets. Therefore, the stenosed sites X1 and X2 can be more effectively treated. In addition, the medical device 100 includes the releasing unit 130 which releases the held drug 10. Therefore, the drug 10 can be administered to the stenosed sites X1 and X2 at a desired timing.

In addition, in the medical device 100, the releasing unit 130 may have the vibrating portion 131 including the oscillator 131a. The vibrating portion 131 is vibrated in a state where the electric signal is applied to the oscillator 131a, thereby vibrating the drug holder 120. Vibration energy generated by the vibrated drug holder 120 can promote decomposition of the drug carrier 123 which carries the drug 10. Accordingly, the drug 10 can be quickly eluted. In addition, the drug 10 can be discharged (sustainably released) to the outside of the drug holder 120 by utilizing the vibrations. Therefore, the drug 10 can be administered to the stenosed site X1 at desired timing.

In addition, in the medical device 100, the medical elongated body 110 may be configured so that the cross-sectional outer shape of the portion inserted into the living body may be substantially circular, and that the cross-sectional diameter D may be 0.2 to 0.5 mm. In this way, the medical elongated body 110 with a relatively smaller cross-sectional diameter may be used. In this manner, the medical elongated body 110 can perform predetermined treatment by being inserted into the narrow blood vessel, for example, such as the retinal artery V1 and the spinal artery V2, into which a medical device is less likely to be inserted. Accordingly, it is possible to provide a very convenient skilled technique.

Figure 12:
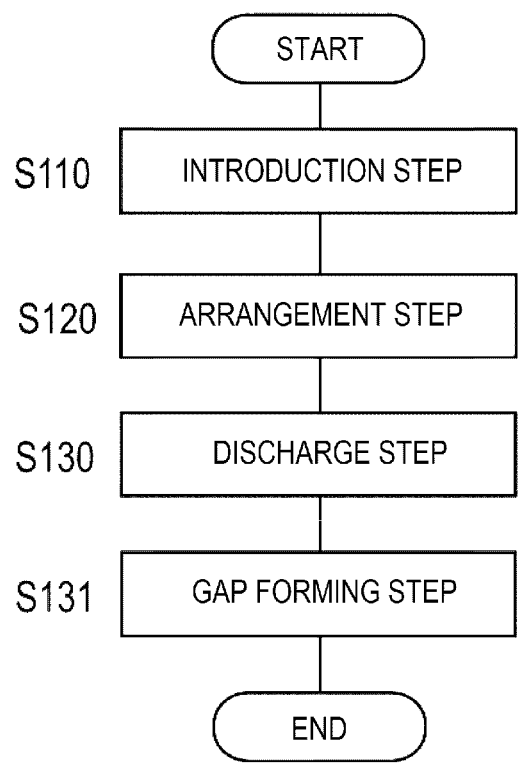
FIG. 12 is a flowchart illustrating a treatment method in accordance with embodiments of the present disclosure.

FIGS. 10 and 11 are views for describing a configuration of each unit of a medical device 200 according to a second embodiment. FIG. 12 is a flowchart illustrating each procedure of a treatment method in accordance with embodiments of the present disclosure. The same reference numerals will be given to configurations which are the same as those according to the above-described embodiments, and description thereof will be omitted.

Referring to FIG. 12, with regard to the discharge step (S130), the treatment method may be different from the embodiments described above. Hereinafter, referring to FIGS. 10 and 11, the medical device 200 used for an embodiment of a treatment method will be described.

As illustrated in FIG. 10A, the medical device 200 may include the medical elongated body 210 that includes a drug holder 220 for holding the drug 10, and that extends in the axial direction, and a releasing unit 230 that releases the drug 10 held by the drug holder 220.

Embodiments of the medical elongated body 210 and the drug holder 220 will be described.

The medical elongated body 210 has a core 211 which extends along the axial direction, and a coil portion 212 which is arranged in a distal portion 211a of the core 211. In addition, the covering layer 113 may be disposed in a portion on the outer surface of the medical elongated body 210.

The coil portion 212 is arranged on the outer periphery of the portion having the drug holder 120 arranged therein. The coil portion 212 is formed in such a way that an elastic linear member 212a is spirally wound around the axis of the core 211.

A material configuring the linear member 212a is not particularly limited as long as the material is elastic in nature. For example, spring steel is an elastic material that can be used.

In the coil portion 212, in a normal state where no external force is applied thereto (refer to FIG. 11A), the spirally wound linear members 212a may be arranged without any gaps disposed therebetween, and the lumen of the coil portion 212 may include an accommodation space 221 which accommodates the drug 10.

The drug holder 120 may be configured to include the accommodation space 221 formed in the lumen of the coil portion 212, and a drug carrier 223 for holding the drug 10. The drug carrier 223 can be configured to have the same material as that of the drug carrier 123 as described above.

As illustrated in FIG. 10D, the drug 10 in a state of being carried by the drug carrier 223 is held in a portion on the outer surface of the distal portion 211a of the core 211.

The releasing unit 230 will be described.

The releasing unit 230 has a first fixing portion 231 arranged on the distal side of the medical elongated body 210, and a second fixing portion 232 arranged on the proximal side.

As illustrated in FIGS. 10B, 10C, and 11A, a distal end 212d of the linear member 212a of the coil portion 212 and a distal end 211d of the core 211 are fixed (fixedly attached) to the first fixing portion 231. In addition, a proximal end 212p of the linear member 212a of the coil portion 212 may be fixed (fixedly attached) to the second fixing portion 232.

A configuration of the second fixing portion 232 is not particularly limited as long as an external force can be applied to the proximal end 212p of the linear member 212a by an operator's hand-side operation. For example, as illustrated in FIG. 11B, a configuration can be adopted which includes a lumen and the second fixing portion 232 is formed in a tube shape extending to the operator's hand-side. The core 211 can be movably inserted into the lumen of the second fixing portion 232.

In addition, an operation lever 233 may be disposed on the proximal side (operator's hand-side) of the second fixing portion 232. The operation lever 233 is operated, thereby enabling the second fixing portion 232 to move relative to the first fixing portion 231.

The second fixing portion 232 is configured to be movable relative to the first fixing portion 231. In some embodiments, as illustrated by an arrow in FIG. 11, the "relative movement" may include rotary movement for rotating the second fixing portion 232 around the axis relative to the first fixing portion 231, and axial movement for moving the second fixing portion 232 to the proximal side relative to the first fixing portion 231.

The method of fixing the coil portion 212 and the core 211 using the first fixing portion 231 and the second fixing portion 232 is not particularly limited. For example, it is possible to use a method such as brazing, soldering, bonding using an adhesive, and welding.

As illustrated in FIG. 11B, in a state where the second fixing portion 232 is moved relative to the first fixing portion 231, in the coil portion 212, a gap 212b which causes the accommodation space 221 and the outside of the coil portion 212 to communicate with each other is formed between the spirally wound linear members 212a. The gap 212b allows the drug 10 to move from the accommodation space 221 to the outside of the coil portion 212.

Next, an embodiment of a treatment method will be described. Referring to FIGS. 3 to 9 and 12, the introduction step (S110) and the arrangement step (S120) may be the same as those described above, and thus, description thereof will be omitted. In addition, the treatment target portions in the living body 400 to which the treatment method is applied may be set to the retinal artery V1 and the spinal artery V2.

Referring to FIG. 12, the discharge step (S130) is performed through the introduction step (S110) and the arrangement step (S120). The discharge step (S130) has a gap forming step (S131) of forming the gap 212b which causes the accommodation space and the outside of the coil portion to communicate with each other by applying an external force to the coil portion 212.

In a state where the introduction step (S110) and the arrangement step (S120) are completed, as illustrated in FIGS. 6B and 9B, the medical elongated body 210 may be inserted into the retinal artery V1 and/or the spinal artery V2 which are the treatment targets. The drug holder 220 is arranged at the stenosed sites X1 and X2. In this way, in a state where the drug holder 220 is arranged at the stenosed sites X1 and X2, the discharge step (S130) is performed.

In the gap forming step (S131), the operation lever 233 may be operated to rotationally move or axially move the second fixing portion 232 relative to the first fixing portion 231 (refer to the arrow in FIG. 11). In this manner, the proximal end 212p of the linear member 212a which is fixed to the second fixing portion 232 moves relative to the distal end 212d of the linear member 212a which is fixed to the first fixing portion 231. Therefore, in the coil portion 212, the gap 212b which causes the accommodation space 221 and the outside of the coil portion 212 to communicate with each other is formed between the spirally wound linear members 212a.

The gap 212b allows the drug 10 to move from the accommodation space 221 to the outside of the coil portion 212. Accordingly, the drug 10 eluted inside the accommodation space 121 is discharged (sustainably released) to the outside of the coil portion 212.

In addition, in the gap forming step (S131), a movement amount of the second fixing portion 232 relative to the first fixing portion 231 is adjusted. In this manner, a size of the gap 212b can be adjusted. A discharge amount of the drug 10 increases as the size of the gap 212b increases. Accordingly, the movement amount of the second fixing portion 232 relative to the first fixing portion 231 is adjusted. In this manner, the discharge amount of the drug 10 can be adjusted.

Next, an operation effect will be described in accordance with embodiments of the present disclosure.

According to a treatment method of the present disclosure, in the discharge step (S130), an external force may be applied to the coil portion 212. The gap 212b which causes the accommodation space 221 and the outside of the coil portion 212 to communicate with each other is formed. The drug 10 is discharged to the outside of the coil portion 212 via the gap 212b.

In the above-described treatment method, after the drug holder 120 is arranged at the stenosed sites X1 and X2, the external force is applied to the coil portion 212. The gap 212b which allows the drug 10 to move from the accommodation space 221 to the outside of the coil portion 212 is formed. According to the treatment method, the drug 10 held by the coil portion 212 is intentionally released, thereby discharging the drug 10 to the stenosed sites X1 and X2. Therefore, the drug 10 can be administered to the stenosed sites X1 and X2 at a desired treatment time. Furthermore, according to the treatment method of the present disclosure, the size of the gap 212b may be adjusted. In this manner, the discharge amount of the drug 10 can be adjusted. Therefore, it is possible to relatively easily control the discharge amount of the drug 10, and it is possible to more effectively treat the stenosed sites X1 and X2 which are the treatment targets.

In the medical device 200, the drug holder 220 has the coil portion 212 in which the elastic linear member 212a is spirally wound around the axis so as to form the accommodation space 221, and in which the drug 10 is accommodated in the accommodation space 221. The releasing unit 230 has the first fixing portion 231 which fixes the distal end (one end) 212d of the linear member 212a, and the second fixing portion 232 which fixes the proximal end (the other end) 212p of the linear member 212a and which is configured to be movable relative to the first fixing portion 231. In a state where the second fixing portion 232 is moved relative to the first fixing portion 231, the gap 212b which causes the accommodation space 221 and the outside of the coil portion 212 to communicate with each other is formed. The gap 212b allows the drug 10 to move from the accommodation space 221 to the outside of the coil portion 212.

According to the above-described medical device 200, a skilled technique using the coil portion 212 which accommodates the drug in the accommodation space 221 is used. In this manner, after the drug holder 120 is arranged at the stenosed sites X1 and X2, the external force is applied to the coil portion 212. Accordingly, it is possible to form the gap 212b which allows the drug 10 to move from the accommodation space 221 to the outside of the coil portion 212. According to the treatment method, the drug 10 held by the coil portion 212 is intentionally released, thereby discharging the drug 10 to the stenosed sites X1 and X2. Therefore, the drug 10 can be administered to the stenosed sites X1 and X2 at a desired treatment time. Furthermore, according to the treatment method of the present disclosure, the size of the gap 212b can be adjusted. In this manner, the discharge amount of the drug 10 can be adjusted. Therefore, it is possible to relatively easily control the discharge amount of the drug 10, and it is possible to more effectively treat the stenosed sites X1 and X2 which are the treatment targets.

Figure 13:
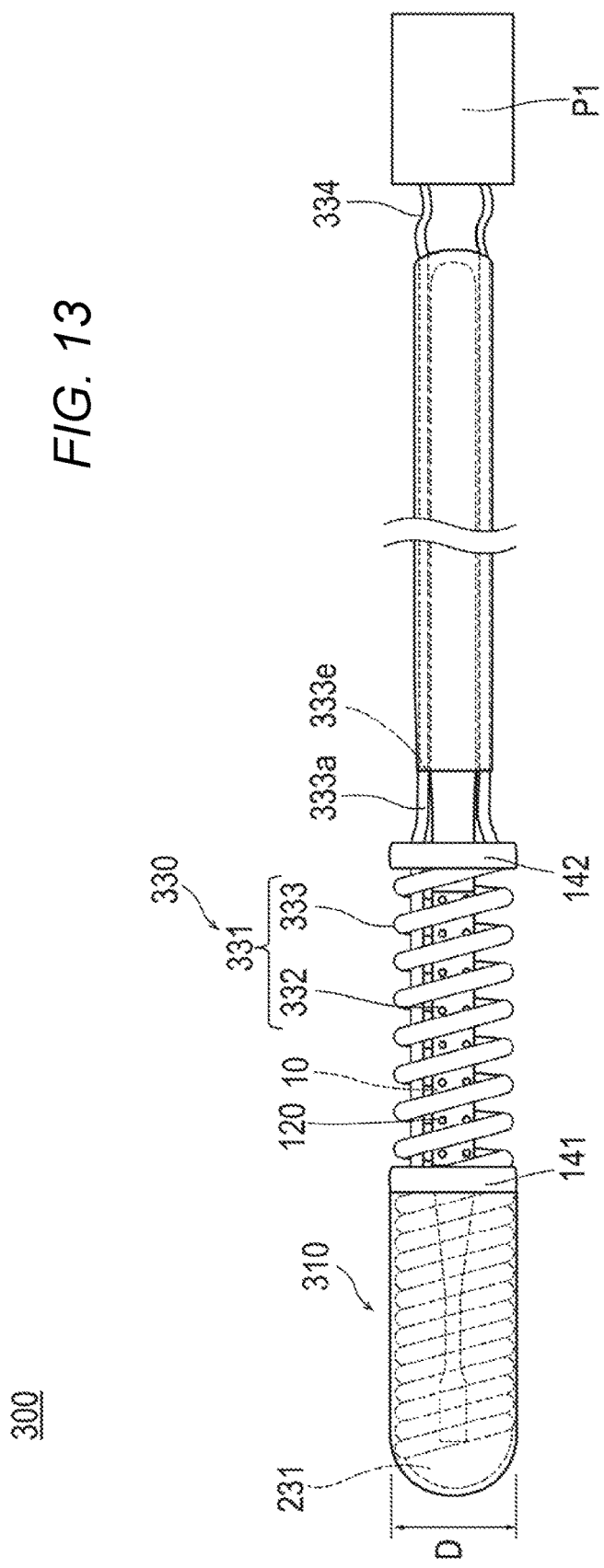
FIG. 13 is a schematic view illustrating a medical device in accordance with embodiments of the present disclosure.
Figure 14:
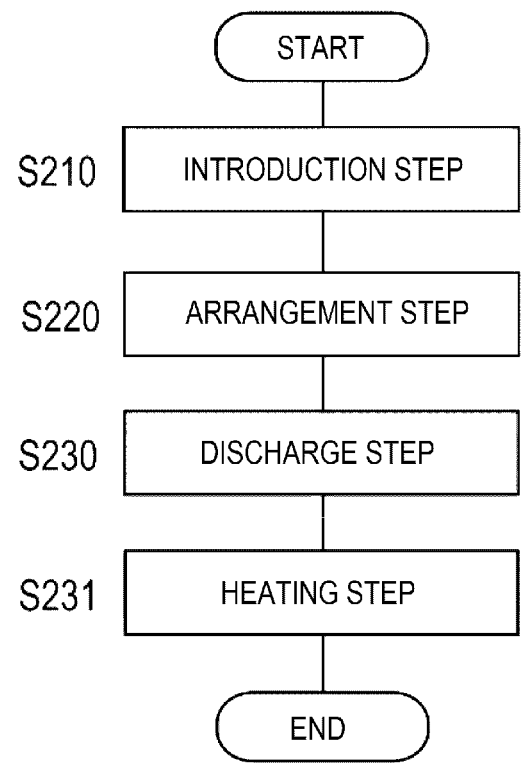
FIG. 14 is a flowchart illustrating a treatment method in accordance with embodiments of the present disclosure.

FIG. 13 is a view illustrating components of a medical device 300 in accordance with embodiments of the present disclosure. FIG. 14 is a flowchart illustrating an embodiment of a treatment method. The same reference numerals will be given to configurations which are the same as those according to the above-described embodiments, and description thereof will be omitted.

Referring to FIG. 14, a discharge step (S230) of an embodiment of the treatment method may be different from the discharge steps described above. Hereinafter, referring to FIG. 13, the medical device 300 used for an embodiment of the treatment method will be described.

In some embodiments, the medical device 300 may include a releasing unit 330 having a heating portion 331 for heating the drug holder 120. The heating portion 331 may be configured to include a core 332 and an induction coil 333 (to be described later), and generates induction heating for at least a portion of the core 332 in a state where power is supplied to the induction coil 333.

The core 332 and the induction coil 333 will be described.

In some embodiments, the core 332 extends along the axial direction of a medical elongated body 310, and includes the drug holder 120 in the distal portion 111a. The core 332 may be formed of a material conducting electricity (electrically conductive material). In the core 332, at least a portion having the drug holder 120 arranged therein may be provided with a magnetic property, and the other portions may not be provided with the magnetic property.

The electrically conductive material configuring the core 332 is not particularly limited. For example, it is possible to use a known metal material or conductive resin material.

The induction coil 333 is arranged in the portion having the drug holder 120 arranged in the core 332. The induction coil 333 is formed in such a way that a linear member 333a formed of the electrically conductive material is spirally wound along the outer peripheral surface of the core 332.

An end portion 333e of the linear member 333a configuring the induction coil 333 is electrically connected to an external device (power source) P1 via another electrically conductive material wire (electric wire) 334. The external device P1 is configured to be capable of supplying electricity to the induction coil 333.

In a state where the electricity is supplied from the external device P1 to supply power to the induction coil 333, the induction coil 333 is subjected to electromagnetic induction for generating a magnetic field in the core 332. The electromagnetic induction generates a current in the core 332, and the core 332 is heated due to electrical resistance. In this way, the core 332 is subjected to induction heating. In this manner, the drug carrier 123 of the drug holder 120 arranged in the core 332 is heated.

As long as the drug holder 120 can be heated, the heating portion 331 is not limited to the above-described configuration in which the drug holder 120 is heated by means of the induction heating.

Next, an embodiment of the treatment method will be described. Referring to FIGS. 3 to 9 and 14, the introduction step (S210) and the arrangement step (S220) may be similar to one or more embodiments previously described, and thus, description thereof will be omitted. In addition, the treatment target portions in the living body 400 to which the treatment method is applied may be set to the retinal artery V1 and/or the spinal artery V2.

Referring to FIG. 14, the discharge step (S230) is performed through an introduction step (S210) and an arrangement step (S220). In the discharge step (S230), a heating step (S231) is performed.

In a state where the introduction step (S210) and the arrangement step (S220) are completed, as illustrated in FIGS. 6B and 9B, the medical elongated body 210 is inserted into the retinal artery V1 and the spinal artery V2 which are the treatment targets, and the drug holder 120 is arranged at the stenosed sites X1 and X2. In this way, in a state where the drug holder 120 is arranged at the stenosed sites X1 and X2, the heating step (S231) is performed as the discharge step (S230).

In the heating step (S231), the drug holder 120 is heated by the heating portion 331. Specifically, in a state where the external device P1 is operated so as to supply power to the induction coil 333, the core 332 is subjected to induction heating by means of the electromagnetic induction. In this manner, heat is transferred from the heated core 332, thereby heating the drug holder 120. A heating temperature may be set to 50° C. to 60° C. in order to prevent the living body 400 from being affected.

As the temperature of the drug carrier 123 of the drug holder 120 becomes higher, the eluting rate at which the drug 10 is eluted becomes higher. For example, in a case where the drug holder 120 is a water-soluble polymer, a soluble degree to a body fluid is accelerated. Accordingly, the heating portion 331 is heated, thereby enabling the drug 10 to be intentionally discharged (sustainably released). In this manner, the elution of the drug 10 is promoted inside the accommodation space 121. The drug 10 can be discharged (sustainably released) to the outside of the accommodation space 121 via the hole portion 122.

Next, an operation effect will be described in accordance with embodiments of the present disclosure.

In embodiments of the treatment method, in the discharge step (S130), the drug 10 may be eluted by heating the drug holder 120. As the temperature of the drug carrier 123 of the drug holder 120 becomes higher, the eluting rate at which the drug 10 is eluted becomes higher. In this manner, the drug 10 can be more quickly eluted. Therefore, it is possible to shorten a time required for a skilled technique.

In one embodiment, the releasing unit 330 has the heating portion 331 for heating the drug holder 120. As the temperature of the drug carrier 123 of the drug holder 120 becomes higher, the eluting rate at which the drug 10 is eluted becomes higher. Accordingly, the drug 10 can be more quickly eluted through the skilled technique using the heating portion 331. Therefore, it is possible to shorten a time required for a skilled technique.

Embodiments of a treatment method and the medical device have been described in accordance with embodiments of the present disclosure. However, the present disclosure is not limited to only the configurations described in the embodiments above, and can be appropriately modified within the scope of the claims.

For example, a skilled technique has been described in which the drug is released from being held by the drug holder by performing any one treatment process of vibrating, forming a gap, and of heating. However, one or more of the above-described treatment processes can be combined with one another. Since multiple treatment processes can be combined, the drug held by the drug holder can be more quickly released.

In addition, the medical device including the releasing unit may include any one of the vibrating portion, the coil portion having the accommodation space for holding the drug, and the heating portion. However, a configuration may include multiple elements combined with one another from the above-described elements. Since the multiple elements can be combined, a skilled technique for releasing the drug held by the drug holder can be more quickly used.

In addition, as long as a configuration enables the drug to be held and to be intentionally released by the releasing unit, the drug holder is not limited to the above-described configurations. For example, the drug holder includes the drug carrier. However, without being limited thereto, a configuration without including the drug carrier may be adopted.

In addition, the sites of the living body to which the described treatment methods and medical devices are applied are not limited to blood vessels such as the retinal artery and the spinal artery, and may include any blood vessel which is a drug-dispensing target inside the living body or other living body organs.

REFERENCE SIGNS LIST

10 DRUG,
100, 200, 300 MEDICAL DEVICE,
110, 210, 310 MEDICAL ELONGATED BODY,
111, 211 CORE,
120, 220 DRUG HOLDER,
121, 221 ACCOMMODATION SPACE,
122 HOLE PORTION,
123, 223 DRUG CARRIER,
130, 230, 330 RELEASING UNIT,
131 VIBRATING PORTION,
212 COIL PORTION,
212b GAP,
231 FIRST FIXING PORTION,
232 SECOND FIXING PORTION,
331 HEATING PORTION,
400 LIVING BODY.

What is claimed is:

1. A treatment method comprising:
an introduction step of introducing a medical elongated body having a drug holder for holding a drug into a living body, wherein the medical elongated body includes a flexible portion comprising a linear member spirally wound around an axis of the medical elongated body, wherein the drug holder is disposed inside the flexible portion, and wherein a plurality of drug discharge holes of the drug holder are arranged along a length of the flexible portion;
an arrangement step of arranging the drug holder at a treatment target inside the living body; and
a discharge step of discharging the drug to the treatment target by releasing the drug held by the drug holder through the plurality of drug discharge holes and then through gaps disposed in between spirals of the flexible portion of the medical elongated body along a length of the drug holder.

2. The treatment method according to claim 1, wherein in the discharge step, the drug is discharged to the treatment target by vibrating the drug holder.

3. The treatment method of claim 2, wherein the medical elongated body comprises a distal portion and a proximal portion, wherein the distal portion includes a vibrating portion including an oscillator configured to vibrate the drug holder.

4. The treatment method of claim 3, wherein the oscillator is disposed at the distal portion of the medical elongated body.

5. The treatment method of claim 3, wherein the vibrating portion vibrates the drug holder when an electric signal is applied to the oscillator.

6. The treatment method of claim 5, wherein the drug is held in a drug carrier material inside the drug holder.

7. The treatment method of claim 5, further comprising:
selectively applying the electric signal to the oscillator thereby controlling the discharging of the drug from the drug holder via controlled vibration of the vibrating portion.

8. The treatment method of claim 7, wherein selectively applying the electric signal includes controlling an amplitude or vibration frequency of the oscillator, wherein an increase in the amplitude or vibration frequency of the oscillator increases an elution rate of the drug, and wherein a decrease in the amplitude or vibration frequency of the oscillator decreases the elution rate of the drug.

9. The treatment method according to claim 1,
wherein the medical elongated body has a cross-sectional outer shape which is substantially circular, and
wherein the cross-sectional diameter is 0.2 to 0.5 mm.

10. The treatment method of claim 1, wherein the medical elongated body includes a first marker disposed on a distal side of the drug holder and a second marker disposed on a proximal side of the drug holder, and wherein the arrangement step comprises:
imaging, via X-ray radiography, the first marker and the second marker inside the living body at the treatment target; and adjusting, using the X-ray radiography imaging, a position of the drug holder inside the living body relative to the treatment target.

11. The treatment method of claim 1, wherein prior to the introduction step the method further comprises:
introducing a guide wire into an artery of the living body;
positioning a distal end of the guide wire inside the artery adjacent to the treatment target;
inserting a sheath having a lumen into the artery of the living body along the guide wire;
positioning a distal end of the sheath inside the artery adjacent to the treatment target; and
removing the guide wire from the artery of the living body while the sheath is maintained in position inside the artery adjacent to the treatment target.

12. The treatment method of claim 11, wherein in the introduction step, the medical elongated body is introduced via the lumen of the sheath while the sheath is maintained in position inside the artery adjacent to the treatment target.

13. A treatment method, comprising:
introducing a medical elongated body having a drug holder into a biological lumen of a living body, wherein the medical elongated body includes a flexible portion formed in a coil shape comprising a linear member spirally wound around the drug holder and an axis of the medical elongated body;
positioning the drug holder at a treatment target inside the biological lumen of the living body; and
discharging a drug held inside the drug holder to the treatment target by releasing the drug through a plurality of drug discharge holes disposed in the drug holder and then through gaps disposed in between spirals of the flexible portion of the medical elongated body, wherein the plurality of drug discharge holes are arranged along a length of the flexible portion.

14. The treatment method of claim 13, wherein the medical elongated body includes a first radiopaque marker disposed on a distal side of the drug holder and a second radiopaque marker disposed on a proximal side of the drug holder, and wherein the drug discharge holes of the drug holder are disposed between the first radiopaque marker and the second radiopaque marker.

15. The treatment method of claim 14, further comprising:
imaging, via X-ray radiography, the first radiopaque marker and the second radiopaque marker inside the living body at the treatment target; and
adjusting, using the X-ray radiography imaging, a position of the drug holder inside the living body relative to the treatment target.

16. The treatment method of claim 15, wherein the medical elongated body comprises a distal portion and a proximal portion, wherein the distal portion includes a vibrating portion including an oscillator configured to vibrate the drug holder and release the drug held therein.

17. The treatment method of claim 16, wherein the oscillator is disposed at the distal portion of the medical elongated body.

18. The treatment method of claim 17, further comprising:
applying an electrical signal, via an electric wire running from a device arranged external to the living body through a lumen of the medical elongated body to the oscillator, that controls a vibration amplitude or vibration frequency produced by the oscillator.

19. The treatment method of claim 18, wherein increasing the vibration amplitude or vibration frequency of the oscillator via the electrical signal increases an elution rate of the drug, and wherein decreasing the amplitude or vibration frequency of the oscillator via the electrical signal decreases the elution rate of the drug.

20. A treatment method, comprising:
introducing a guide wire into a biological lumen of a living body;
positioning a distal end of the guide wire inside the biological lumen adjacent to a treatment target inside the living body;
inserting a sheath having a lumen into the biological lumen of the living body along the guide wire;
positioning a distal end of the sheath inside the biological lumen of the living body adjacent to the treatment target;
removing the guide wire from the biological lumen of the living body while the sheath is maintained in position inside the biological lumen adjacent to the treatment target;
introducing a medical elongated body having a drug holder into the biological lumen of the living body through the lumen of the sheath, wherein the medical elongated body includes a flexible portion formed in a coil shape comprising a linear member spirally wound around the drug holder and an axis of the medical elongated body;
positioning the drug holder at the treatment target inside the biological lumen of the living body; and
discharging a drug held inside the drug holder to the treatment target by releasing the drug through a plurality of drug discharge holes disposed in the drug holder and then through gaps disposed in between spirals of the flexible portion of the medical elongated body, wherein the plurality of drug discharge holes are arranged along a length of the flexible portion.

* * * * *